United States Patent [19]

Parthasarathy et al.

[11] 4,410,726
[45] Oct. 18, 1983

[54] VINYLATION REACTION

[75] Inventors: R. Parthasarathy; Eugene V. Hort, both of Wayne; Paritosh M. Chakrabarti, Cedar Grove, all of N.J.

[73] Assignee: GAF Corporation, New York, N.Y.

[21] Appl. No.: 273,178

[22] Filed: Jun. 12, 1981

[51] Int. Cl.³ .................... C07D 207/263; B01J 31/12
[52] U.S. Cl. .............................. 548/543; 260/239.3 R; 546/243; 502/156
[58] Field of Search ................. 260/326.5 F, 239.3 R; 546/243; 548/543; 252/431 N

[56] References Cited

U.S. PATENT DOCUMENTS

| | | | |
|---|---|---|---|
| 2,317,804 | 4/1943 | Reppe et al. | 260/239.3 R |
| 2,806,847 | 9/1957 | Nedwick | 260/239.3 R |
| 2,806,848 | 9/1957 | Nedwick | 260/239.3 R |

*Primary Examiner*—Mark L. Berch
*Assistant Examiner*—D. B. Springer
*Attorney, Agent, or Firm*—Marilyn J. Maue; J. Gary Mohr; Joshua J. Ward

[57] ABSTRACT

The present invention relates to an improved method for the vinylation of pyrrolidone with acetylene in the presence of an alkali metal salt of said pyrrolidone as a catalyst, by the addition of between about 0.2 and about 8 weight-%, based on total feed, of a polyoxyalkylene glycol; a polyoxyalkylene phenol, optionally substituted with an alkyl group; a polyoxyalkylene ether or mixtures thereof; said polyoxyalkylene compound having a number average molecular weight of between about 175 and 2,000 and containing between 4 and 40 oxyethylene and/or oxypropylene units. The invention also pertains to a novel coacting catalyst composition for use in vinylation reactions comprising said alkali metal salt of said pyrrolidone in admixture with said polyoxyalkylene compound.

13 Claims, No Drawings

VINYLATION REACTION

The vinylation of lactams with acetylene in the presence of strongly alkaline derivatives is well-known and is exemplified in U.S. Pat. Nos. 2,806,847 and 2,806,848. In the preparation of N-vinylpyrrolidone, a substantial portion of non-volatile polymeric residue is formed during the reaction which represents a significant yield loss and complicates the separation and recovery of the desired product. Accordingly, prior processes have resorted to restricting conversion of pyrrolidone to low levels as a means of minimizing polymeric residue formation. However, even at the sacrifice of high conversion, the residue continues to form at an undesirably high level.

Accordingly, it is an object of this invention to overcome the above difficulties by means of an economically feasible process for vinylation of pyrrolidone. Another object is to form less polymeric residue and to provide a novel co-catalyst for improving efficiency in vinylation reactions.

Still another object is to provide a process for producing N-vinylpyrrolidone in higher yield by the reaction of acetylene with pyrrolidone.

These and other objects will become apparent from the following description and disclosure.

According to this invention pyrrolidone is contacted with acetylene in the presence of between about 0.5 and about 5 weight-% of a catalyst comprising an alkali metal salt of pyrrolidone and between about 0.25 and about 8 weight-%, based on total feed, of a polyoxyalkylene co-catalyst containing oxyethylene and/or oxypropylene units and having a number average molecular weight between about 175 and about 2,000, which compound is selected from the group consisting of a polyoxyalkylene glycol, a polyoxyalkylene ether or a polyoxyalkylene phenol optionally substituted with an alkyl group.

Representative of the polyoxyalkylene compounds which are suitably employed as co-catalysts in the present invention are the polyoxyethylene- or polyoxypropylene-phenols and mixtures thereof; the polyoxyethylene- or polyoxypropylene-glycols and mixtures thereof; the polyoxypropylene- or polyoxyethylene-alkylphenols wherein the alkyl group contains from 1 to 24 carbon atoms, and mixtures thereof; which polymeric co-catalysts preferably contain from 6 to 36 oxyalkylene units as homopolymers or mixed oxyethylene and oxypropylene copolymers of random or block structure, and have a number average molecular weight of between about 240 and about 1400. The eithers of polyoxyalkylenes include crown ethers containing 4, 6 or 8 oxygen atoms in the cyclic structure.

The preferred group of co-catalysts includes the 18 membered ring crown ether of polyoxyethylene having 6 oxygen atoms, the alkyl phenol terminated polyoxyethylene wherein the alkyl substituent contains from 6 to 12 carbon atoms, having the formula:

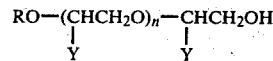

A where n has a value of 6 to 18, and polyoxyethylene- and/or polyoxypropylene-glycols, i.e.

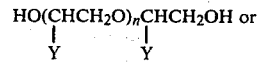

B

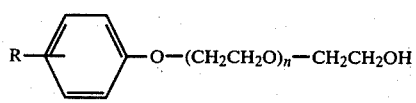

where n has a value of 6 to 18 and Y is hydrogen or methyl and R is alkyl of 1 to 20 carbon atoms and intermixtures thereof.

The alkali metal salt of pyrrolidone preferably the potassium or sodium salt, can be directly introduced into the reaction mixture or it may be produced in situ by reacting the lactam with between about 0.5 and about 5 weight-% of the corresponding alkali metal hydroxide at a temperature between 75° C. and about 130° C. while removing the water of reaction under reduced pressure.

In a preferred embodiment, the lactam, the alkali metal hydroxide and the polyoxyalkylene co-catalyst are mixed and refluxed for a period of from about 0.5 to about 3 hours under reduced pressure with continuous removal of water. If desired, the catalyst composition can be preformed by mixing the required amounts of polyoxyalkylene compound, alkali metal hydroxide any pyrrolidone or by mixing the required amount of polyoxyalkylene compound with the pyrrolidone alkali metal salt before refluxing to remove water. Alternatively, if desired, the co-catalyst can be added to the reaction mixture of pyrrolidone and pyrrolidone alkali metal salt after refluxing; although for best results refluxing the entire mixture is recommended to insure complete removal of water before vinylation.

In the present reaction, the pyrrolidone salt catalyst comprises between about 0.5 and about 5% by weight, preferably between about 0.8 and about 3% by weight of the reaction mixture. The polyoxyalkylene compound is present in an amount, between about 0.25 and about 8% by weight, preferably between about 0.8 and about 7% by weight. Most desirably between about 1 and about 5% by weight of the co-catalyst, based on total feed, is employed.

The present vinylation reaction with the aid of the co-catalyst is carried out under substantially anhydrous conditions and under from about 4 to about 20 atmospheres acetylene partial pressure, at a temperature of from about 100° C. to about 160° C., preferably under an acetylene partial pressure of from about 6 to about 15 atmospheres at between about 115° C. and about 155° C., until about 45% to about 85%, preferably 50 to 75%, vinylation takes place, which reaction usually requires 6 to 12 hours. A significantly reduced amount of non-volatile polymeric residue forms as a by-product of the reaction and is easily separated by distillation from the volatile products which include vinyl pyrrolidone and unconverted pyrrolidone. The pyrrolidone can be recovered from vinylated product by fractional distillation under reduced pressure and conveniently recycled.

As a consideration for safety, the acetylene reactant is introduced into the reaction mixture in a diluted state, preferably in admixture with an inert gas such as nitrogen, a saturated light hydrocarbon, e.g. propane or butane. The acetylene gas mixture is introduced incrementally during the course of the synthesis to satisfy the requirements of the reaction. The resulting mixture is then agitated and reacted under the above reaction conditions to produce the desired product.

Operation under the above conditions minimizes the formation of non-volatile by-product, which is comprised mainly of polymers containing vinyl pyrrolidone and pyrrolidone moieties and can provide selectivities to N-vinyl pyrrolidone product higher than 90%.

While the present invention is not limited to any chemical theory, it is believed that the higher selectivity results from the ability of the polymeric co-catalyst to effect the separation of charges surrounding the cation of the pyrrolidone salt so that a more efficient vinylation results. The mechanism of the reaction is illustrated by the following equations, C(a)-(c), where it will be appreciated that as the separation of $N^\ominus$ and $K^\oplus$, increases, vinyl substitution is facilitated. The separation of the charges is effected by the ability of the polyoxyalkylene chain to surround the alkali metal ion; thus, permitting entry and reaction of the acetylene molecule at the site of the cation. The present process achieves additional benefit from the mild reaction conditions which lessen the formation of polymeric materials.

According to the present invention, the vinylation which ensues is believed to pass through the following sequence of stages.

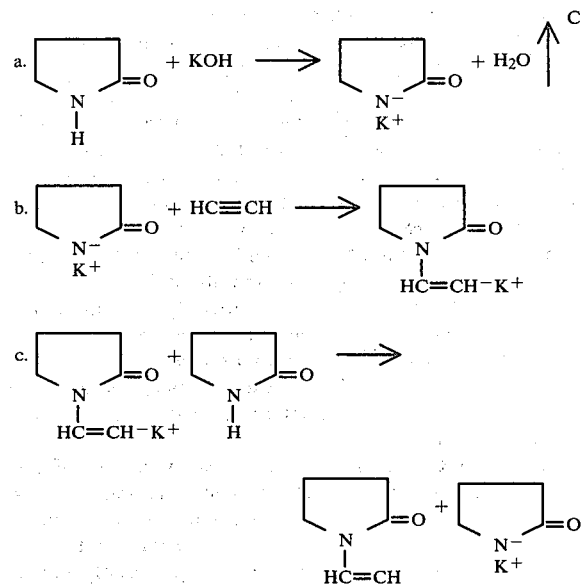

After the desired amount of reaction has taken place, the product mixture is stripped of volatile material under vacuum whereupon vinylpyrrolidone and unconverted pyrrolidone are separated from the polymeric by-product residue. The volatile material is fractionally distilled to separate vinyl pyrrolidone from unreacted pyrrolidone. The unreacted pyrrolidone can be recycled to catalyst preparation or vinylation to provide an overall complete conversion of pyrrolidone. Such a process can be effected as a continuous or a batch operation.

Having thus described the invention, reference is now had to the accompanying examples which provide preferred embodiments but which are not to be construed as to limiting the scope of the invention which is more generally described above and which is particularly set forth in the appended claims.

In the following examples all amounts are by weight unless otherwise indicated.

EXAMPLES 1-9

Into a reflux vessel, containing 100 g. of 2-pyrrolidone, was introduced a mixture of KOH 85% pellets (commercial grade) and co-catalyst in amounts specified in following Table I. This mixture was refluxed at 115°-120° C. for 1 hour under reduced pressure while gently sparging with nitrogen and removing water of reaction. The resulting charge was then transferred to an autoclave reactor, to which acetylene was introduced as a 50/50 mixture with nitrogen. The reactor is maintained at the elevated temperature and partial pressure of acetylene indicated in Table I for about 10 hours, until the vinylation reached 47-62% conversion of lactam to vinyl pyrrolidone, after which the product mixture was removed and separated by vacuum distillation. The distillate containing vinyl pyrrolidone and unconverted 2-pyrrolidone was analyzed by gas chromatography and the yields of product and non-volatiles are reported in Table I.

In these examples, polyoxypropylene glycols or alkylphenol terminated polyoxypropylene glycols can be substituted to provide similar beneficial effects. Also, mixed polyoxyethylene-polyoxypropylene co-catalysts can be beneficially substituted in these examples.

When the sodium salt of the lactam, prepared as described above with substitution of NaOH for KOH, replaces the catalyst portion of the catalytic composition, similar beneficial results in the diminution of non-volatile residue is obtained.

TABLE

VINYLATION OF 2-PYRROLIDONE
N—Vinyl Pyrrolidone Yield Improvement Using Various Co-Catalysts

| Example | Co-Catalyst | Wt-% KOH based on feed | Wt-% co-catalyst based on feed | Vinylation °C./psig | Vinylpyrrolidone in distillate Wt-% | Residue Wt-% of vinylpyrrolidone produced* | Yield vinylpyrrolidone % of theory |
|---|---|---|---|---|---|---|---|
| 1 | 18-Crown polyoxyethylene of 6 oxygen atoms | 0.5 | 2.5 | 150/150 | 50.1 | 3.2 | 95 |
| 2 | Igepal CO-630 (1) | 0.9 | 1.0 | 140/110 | 62.3 | 6.2 | 92 |
| 3 | Igepal CO-630 | 1.0 | 4.6 | 140/100 | 57.2 | 4.5 | 94 |
| 4 | Igepal CO-850 (2) | 0.9 | 1.0 | 140/110 | 54.7 | 5.9 | 93 |
| 5 | Igepal CO-850 | 1.0 | 6.4 | 140/100 | 58.9 | 5.7 | 92 |
| 6 | Carbowax PEG 400 (3) | 0.9 | 1.0 | 140/110 | 48.7 | 5.5 | 92 |
| 7 | Carbowax PEG 1000 (4) | 0.9 | 1.0 | 140/110 | 53.6 | 6.5 | 91 |
| 8 | None | 2 | 0 | 115/150 | 58.9 | 9.7 | 88 |

TABLE-continued
VINYLATION OF 2-PYRROLIDONE
N—Vinyl Pyrrolidone Yield Improvement Using Various Co-Catalysts

| Example | Co-Catalyst | Wt-% KOH based on feed | Wt-% co-catalyst based on feed | Vinylation °C./psig | Vinylpyrrolidone in distillate Wt-% | Residue Wt-% of vinylpyrrolidone produced* | Yield vinylpyrrolidone % of theory |
|---|---|---|---|---|---|---|---|
| 9 | None | 0.9 | 0 | 140/110 | 46.9 | 9.8 | 88 |

(1) Supplied by GAF Corp. - polyoxyethylene (average 9 units) terminated at one end with alkylphenol
(2) Supplied by GAF Corp. - polyoxyethylene (average 10 units) terminated by alkylphenol
(3) Supplied by Union Carbide Corp. - polyoxyethylene (10 units)
(4) Supplied by Union Carbide Corp. - polyoxyethylene (23 units)
*exclusive of catalyst or co-catalyst

EXAMPLE 10

In the above examples, the catalyst/co-catalyst composition can be separately prepared by mixing 10 g. of pyrrolidone with 0.5 g. of KOH and 1 to 4 grams of co-catalyst, e.g. 2 g. of Igepal CO-630 and refluxing as described or by mixing 1 g. of the potassium salt in 10 g. of pyrrolidone with, e.g. 2 g. of Igepal CO-630, and adding either of these mixtures to about 90 g. of pyrrolidone in the catalyst preparation vessel. The results achieved are the same as reported in Table I.

EXAMPLE 11

The general procedure described for Example 1 was repeated, except that the catalyst composition was 1 weight-% of KOH catalyst/4 weight-% co-catalyst (based on total feed), the reaction temperature was maintained at 115° C. and the vinylation was allowed to run to 78.6% conversion to vinyl pyrrolidone. In this case, the % yield of theory of vinyl pyrrolidone was 94 while the residue was only 4.8 weight-%.

Many variations and substitutions in the above examples will become apparent to those skilled in the art from the present disclosure; however such modifications are within the scope of the present invention. Accordingly, any of the above described co-catalysts can be employed for vinylation within the parameters of temperature and pressure hereinabove discussed and can be substituted in the above Examples 1–7 and 11.

What is claimed is:

1. A vinylation catalyst composition for use in the vinylation of pyrrolidone with acetylene consisting essentially of a sodium or potassium salt of pyrrolidone as a catalyst and an effective co-acting catalytic amount of a polyoxyalkylene compound selected from the group consisting of a compound having the formula

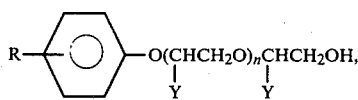

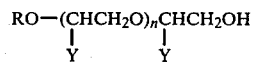

or a crown ether having the formula

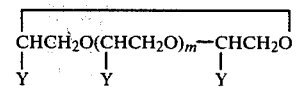

wherein
R is hydrogen or alkyl of from 1 to 24 carbon atoms;
Y is hydrogen or methyl;
n has a value of 6 to 36 and
m has a value of 2, 4 or 6.

2. The composition of claim 1 wherein said polyoxyalkylene compound is a crown ether having 4, 6 or 8 oxygen atoms.

3. The composition of claim 2 wherein said polyoxyalkylene is an 18 membered ring crown ether having 6 oxygen atoms.

4. The composition of claim 2 wherein the polyoxyalkylene is composed of oxyethylene units.

5. The composition of claim 1 wherein said polyoxyalkylene compound is composed of oxyethylene units terminated at least one end by a phenoxy radical optionally substituted by alkyl having from 1 to 24 carbon atoms.

6. The composition of claim 1 wherein said polyoxyalkylene compound is composed of oxyethylene units terminated by an alkyl group having from 1 to 24 carbon atoms.

7. The composition of claim 1 wherein said polyoxyalkylene compound is composed of oxyethylene units terminated by a hydroxyl group.

8. The composition of claim 1 wherein said catalyst is N-potassium-2-pyrrolidone.

9. In the process for vinylating pyrrolidone with acetylene in the presence of a catalytic amount of an alkali metal salt of said pyrrolidone, at a temperature between about 100° and about 160° C. under from about 4 to about 20 atmospheres pressure; the improvement which comprises adding a catalytic promotional amount of a polyoxyalkylene compound of claim 1.

10. The process of claim 9 wherein said polyoxyalkylene compound is added in an amount of between about 0.25% and about 8% by weight, based on total feed.

11. The process of claim 9 wherein the polyoxyalkylene compound is a polyoxyethylene crown ether having 6 oxygen atoms.

12. The process of claim 9 wherein the polyoxyalkylene compound is a polyoxyethylene compound having an average of 9 or 10 oxyethylene units and terminated at one end with an alkyl phenoxy group.

13. The process of claim 9 wherein the polyoxyalkylene compound is a polyoxyethylene glycol having an average of 10 to 23 oxyethylene units.

* * * * *